(12) United States Patent
Yu et al.

(10) Patent No.: US 7,101,841 B2
(45) Date of Patent: Sep. 5, 2006

(54) CARBOHYDRATE-SPECIFIC PEPTIDES WHICH HAVE A STRONG AFFINITY AND PREPARATIONS METHOD THEREOF

(75) Inventors: Jaehoon Yu, Seoul (KR); Miyun Kwon, Seoul (KR); Sunjoo Jeong, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 160 days.

(21) Appl. No.: 10/474,667

(22) PCT Filed: Dec. 5, 2001

(86) PCT No.: PCT/KR01/02102

§ 371 (c)(1),
(2), (4) Date: Oct. 14, 2003

(87) PCT Pub. No.: WO02/083718

PCT Pub. Date: Oct. 24, 2002

(65) Prior Publication Data

US 2004/0176280 A1    Sep. 9, 2004

(30) Foreign Application Priority Data

Apr. 17, 2001 (KR) .............................. 2001-20421

(51) Int. Cl.
  *A01N 37/18* (2006.01)
  *A61K 38/00* (2006.01)
(52) U.S. Cl. .......................................... 514/2; 530/300
(58) Field of Classification Search ............... None
  See application file for complete search history.

(56) References Cited

FOREIGN PATENT DOCUMENTS

WO    WO 94/07517    4/1994

OTHER PUBLICATIONS

Tam, JP., 1996, J. Immunol. Methods, 196, 17-32.*
Tam, JP., Journal Immunological Methods, 1996, 196, 17-32.*
Ravindranath, et al., Cancer, 1997, 79, 1686-1697.*
Dean, JW, The Journal of Biological Chemistry, 1990, 265, 12553-12562.*
An article entitled "Generation of C-Glycoside Peptide Ligands for Cell Surface Carbohydrate . . . ," By Sutherlin et al., published by J. Org. Chem. 1996, vol. 61, pp. 8350-8354.

* cited by examiner

*Primary Examiner*—Bruce R. Campell
*Assistant Examiner*—Satyanarayana R. Gudibande
(74) *Attorney, Agent, or Firm*—Bachman & LaPointe, P.C.

(57) ABSTRACT

The present invention relates to carbohydrate-specific peptides, which have a strong affinity and preparation method thereof. Particularly, the present invention relates to carbohydrate-specific peptides, which have been developed to have an increased strong affinity to carbohydrates by the multiple combinations of peptides having carbohydrates-specific amino acid sequences and preparation method thereof. Carbohydrate-specific peptides of the present invention have a very strong affinity under micromol, so that they can shut off recognition between cells transferred by specific carbohydrates, which means they can be used for the treatment of diseases mediated by recognition between cells and used as a diagnostic kit which diagnoses diseases by confirming the existence of any specific carbohydrate.

7 Claims, 2 Drawing Sheets

CARBOHYDRATE-SPECIFIC PEPTIDES WHICH HAVE A STRONG AFFINITY AND PREPARATIONS METHOD THEREOF

FIELD OF THE INVENTION

The present invention relates to carbohydrate-specific peptides, which have a strong affinity and preparation method thereof. Particularly, the present invention relates to carbohydrate-specific peptides, which have been developed to have an increased strong affinity to carbohydrates by the multiple combinations of peptides having carbohydrates-specific amino acid sequences and preparation method thereof. Carbohydrate-specific peptides of the present invention have a very strong affinity under micromol, so that they can shut off recognition between cells transferred by specific carbohydrate, which means they can be used for the treatment of diseases mediated by recognition between cells and used as a diagnostic kit which diagnoses diseases by confirming the existence of any specific carbohydrate.

BACKGROUND ART OF THE INVENTION

Every cell surfaces of the higher animals are treated with carbohydrates. It has been regarded so far that the role of those carbohydrates is just to protect cell surfaces. However, recent studies have clarified that the structures of those carbohydrates are cell-specific and those carbohydrates play a very important role in recognition between cells (Lis, H. and Sharon, N., Chem. Rev., 1998, 98, 637–674).

Transmitting signals by recognition between cells is highly important to keep an individual stable. Especially, the defense mechanism of human is under the control of recognition between immune cells. Studies have been reported that inflammation, one of human defense mechanism, is caused by specific carbohydrates on cell surfaces and peptides recognizing thereof. Besides, recognition between cells mediated by specific carbohydrates is proven to be essential for metastasis process of cancer, which leads cancer to be a very difficult fatal disease (Fukushima, K., et al., Cancer Res., 1984, 44, 5279–5285; Hanski, C., et al., Cancer Res., 1995, 55, 9280933; Ura, H., et al., World J. Surg., 1997, 21, 773–776).

Though it is not easy to find out the structures of specific carbohydrates on cell surfaces biologically or chemically, it has been successfully found out that one of the carbohydrates specific to cancer cells is sialyl Lewis X (sLeX), an oligosaccharide connected with 4 pyranosides and sLeX along with selectin, a carbohydrate-specific peptide, leads binding between cells (Bertozzi, C. R., Chem. Biol., 1995, 2, 703–708; Lasky, L. A., Science, 1992, 266, 964–968).

The binding power between carbohydrates and selectin is weak at the level of millimolar, but the next joining with integrin, a kind of peptide, produces a strong binding power at the level of micromolar or submicromolar, which is enough power to induce binding and recognition between cells. Since binding and recognition between cells start with recognition between peptides, preparing a subject which controls such recognition can be a basic step for the treatment of diseases caused by recognition between cells.

Studies have been made so far to produce a subject, which can recognize carbohydrates on cell surfaces, but it is still difficult to prepare strong neutralizing molecules. The reason is firstly that carbohydrates have a structure moving freely. Particularly, the hexagon ring of pyranoside can be transformed to a totally different conformation by ring flip and those hexagonal carbohydrates are bound each other with glycosidic bond (C—O—C), which makes it possible to have various different structures. Secondly, it is difficult to recognize carbohydrate molecules because those molecules consist of monosaccharides having similar structures each other. Thirdly, it is very difficult to prepare a carbohydrate-specific antibody since carbohydrate molecules are self-molecules, which hardly evoke antigen-antibody reaction by immune system.

Those reasons are holding scientists not to make a progress of their studies on neutralizing molecules of carbohydrates though carbohydrates are very important target molecules for cell recognition. As a matter of fact, the intensity of binding power of joining or neutralizing molecules is still at low level of mM.

To solve the above problems, the present inventors have developed joining molecules, which can recognize sialyl Lewis X and be bound multiply. Precisely, the present inventors have found peptides, which can bind specifically with sialyl Lewis X using phage display method and prepared those peptides possible for multiple binding in order to increase their low affinity. As a result, peptides, which are bound with specific sialyl Lewis X of the present invention, are confirmed to be joining molecules having a strong affinity under micromol. On the basis of the point that those peptides can recognize carbohydrates specifically connected to cancer cell surfaces, the present inventors have accomplished the present invention by confirming that those peptides can be used for the treatment of diseases mediated by recognition between cells owing to their ability to shut off the recognition between cells mediated by specific carbohydrates and also can be used as a carbohydrate-specific peptides for diagnostic kit, which can diagnoses by confirming the existence of any specific carbohydrate.

SUMMARY OF THE INVENTION

It is an object of the present invention to provide carbohydrate-specific peptides having a multiple structure and a strong affinity under micromol, and preparation method thereof.

It is another object of the present invention to provide a method to use the above carbohydrate-specific peptides for the diagnosis and the treatment of diseases mediated by recognition between cells of specific carbohydrates.

It is further object of the present invention to provide a diagnostic kit, which can diagnose diseases by the existence of specific carbohydrates using the above carbohydrate-specific peptides.

Solid line: sLeX-BSA fixed chip,
Dotted line: BSA fixed chip (control)

Figure 2:
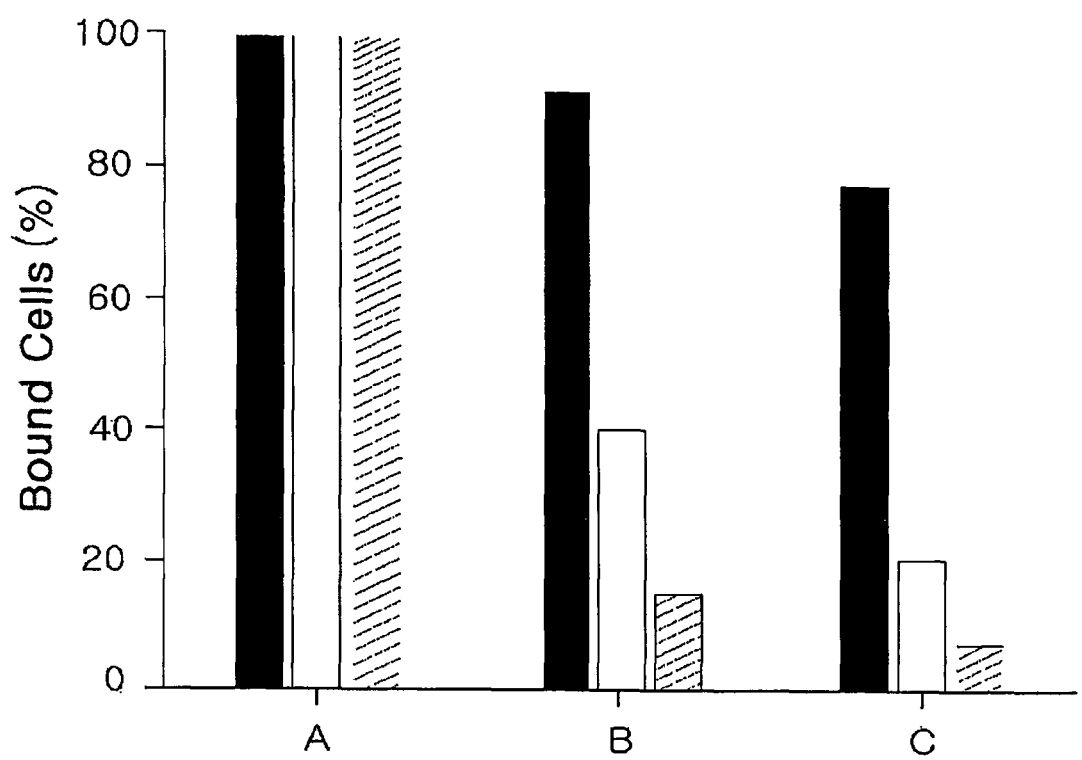

FIG. 2 is the graphs showing the inhibition effect of binding P-selectin with HL-60 cells by the peptides of the present invention.

A: Peptides are not added (control),
B: 3 µg of peptide is added,
C: 5 µg of peptide is added,
■: compared peptides,
□: dimer, ▨: tetramer

DETAILED DESCRIPTION OF THE INVENTION

To achieve those objects, the present invention provides carbohydrate-specific peptides having a multiple structure and a strong affinity under micromol, and preparation method thereof.

The preparation method thereof consists of following steps:
1) Finding peptides which are binding specifically to carbohydrates existing on cell surfaces;
2) Preparing multiplex of the above peptides.

Carbohydrates on cell surfaces of the above step 1) can be a carbohydrate compound as a cancer marker and be selected from the group consisting of sialyl Lewis X (sLeX), Lewis X (LeX), sialyl Lewis A (sLeA) and Lewis A (LeA).

In order to find out peptides binding specifically to carbohydrates on cell surfaces, phage display method, position scanning method and deconvolution method can be used according to the type of peptide library. And in order to prepare multiple-structure to increase the affinity to carbohydrates, lysine and ornitine, a lysine derivative can be used. Multiple-complex can be constructed by binding peptides to amino acid having a strong nucleophilicity and/or amino acid having more than two amino groups like polyamine. Before preparing multimer, peptide dimer has to be prepared using intermediate whose N-terminal has two free amino groups during the synthetic process. In order to prepare tetramer, two lysine layers should be used and using three lysine layers leads to a polypeptide in which 8 peptides are connected like octopus arms. The multimer peptides have stronger affinity than monomer peptides do.

The present invention also provides a method to use the above carbohydrate-specific peptides for the diagnosis and the treatment of diseases mediated by recognizing a specific carbohydrate between cells.

According to the preparation method of the present invention, compounds having a strong affinity of micromol or under micromol to the carbohydrate having very flexible structure can be prepared. As of today, a compound bound to carbohydrates has an over mM affinity. Taking this into consideration, the affinity of the peptides of the present invention is remarkably strong, which can be used in variety.

Carbohydrate-specific molecules can be used for the treatment of diseases mediated by recognition between cells because these molecules can shut off the recognition concerning a specific carbohydrate between cells. The improvement of peptides results in the precaution of hydrolysis of peptides by the peptide hydrolase in vivo. Metastases of cancer, immune-diseases, inflammation, etc., so called the diseases caused by recognition between cells, are very difficult to be cured. Thus, peptides, which are able to recognize a specific carbohydrate directly, can be very good in use for the treatment of such diseases, especially for the effective prevention of cancer metastasis.

In addition, peptides of the present invention can be used as a carbohydrate-recognizing peptide for diagnostic kit, which can diagnose diseases by confirming the existence of specific carbohydrates. Especially, the amount of specific carbohydrates on cell surfaces increases when normal cells are turned to abnormal. Therefore, carbohydrate-recognizing peptides can play an important role in differentiating abnormal cells from normal ones. The improved strong affinity of peptides of the present invention makes it possible to distinguish target cells even if the cells are few or carbohydrates are not widely distributed on cell surfaces. Thus, cancer cells can be detected at the early stage with those peptides and such an early stage diagnosis is believed more important than later treatment.

The present invention provides carbohydrate-specific peptides constructed with amino acid sequence represented by the SEQ. ID. NO: 1, recognizing specific carbohydrates on cancer cells and having an affinity under micromol by multiple structure.

The present inventors have chosen peptides using peptide phage library and biopanning method, which are constructed with 12 amino acid sequence represented by the SEQ. ID. NO: 1 and show relatively strong affinity to sialyl Lewis X (sLeX), a 4-carbon carbohydrate, existing on cancer cells or inflammation cells, and prepared thereof by automatic peptide synthesizer.

Generally, the basic reactions in vivo are derived from the recognition between molecules. As a matter of fact, all medicines used so far are the small molecules interrupting recognition between molecules. The best example for that is antigen-antibody reaction. When an antigen infiltrates into individual, the individual produces antibodies with huge amount to neutralize the antigen. At this time, antibodies need to have a strong affinity to recognize antigen effectively, for which multiple combination is needed. In other words, the antibody has lots of same antigen binding sites, resulting in the induction of powerful binding. For example, IgM antibody has stronger affinity than that of IgG because IgM contains 10 antigen-binding sites while IgG contains 2 antigen-binding sites.

Lots of proteins, which are connected to the signal transduction in vivo, have the structure of dimer, trimer or tetramer and exchange signals between molecules effectively. Carbohydrate-specific peptides have also been confirmed to have those multi-structures. Particularly, in case of carbohydrates on cell surfaces, many molecules are forming domain, which are recognized by carbohydrate-recognizing peptides. The affinity of selectin, which firstly recognizes cell surface carbohydrates is increased remarkably if the carbohydrates are turned to be multiple complex on the surfaces. It is confirmed that integrin which also recognizes carbohydrate and induces a strong affinity by tandem repeat of peptide, has been proved to be related with recognizing the carbohydrates having the above structures. It has been observed that the affinity of integrin lacking in tandem repeat is decreased greatly (Arata, Y., et al., J. Biol. Chem., 1997, 272, 26669–26777).

The tandem repeat is seen not only in the surface proteins of higher animals but also in those of parasites such as *Tripanozoma cruzi* or microorganisms such as *micoplasma pneumaniae*. Amino acid sequence homology of tandem repeat between species is not high, but the most of tandem repeats are consist of 7–12 amino acids. The tandem repeat of lectin in higher animals recognizes target molecules to mediate recognition between cells. Meanwhile the tandem repeat of lectin in parasites is known to be essential for the recognition and binding with cell surface carbohydrates of hosts. Conclusively, the tandem repeat is a necessary structure for peptides to find target carbohydrates, and its repeat cycle includes three at the least to ten, which seems to be a major way to reinforce the recognition to carbohydrates.

To increase the affinity of peptides to carbohydrates, the present inventors tried to prepare 12-amino acid peptides having tandem repeat. Octopus-arm shaped tandem repeat of peptides is more effective to improve their affinity than a solid line tandem repeat, so the present inventors prepared peptides as follows to accomplish that effect. Two amino groups of lysine were used to construct peptides at both sides. At this time, tetramer will be made if two layers of lysine are used and the peptides in which 8 peptides are connected each other like octopus arms will be prepared if three layers of lysine are used. With the above method, multi-binding can be accomplished easily when each peptide recognizes carbohydrates, and also multiple-peptides can be prepared economically.

It is confirmed with the above process that peptides of the present invention showed more increased affinity to carbohydrates when they have dimer or tetramer structure than they have monomer structure (see Chemical Formula 1 to 3).

The present invention also provides a method to use the carbohydrate-specific peptides having a reinforced affinity for the treatment of diseases mediated by recognition between cells and for the diagnosis of diseases by confirming the existence of specific carbohydrates.

The present invention has confirmed that the above peptides having a reinforced affinity under in vitro experiment can control the recognition between cells by binding more preferably to the specific carbohydrates on cancer cells than selectin, an original cancer cell binding peptide.

Therefore, carbohydrate-specific peptides of the present invention can be used for the treatment of diseases mediated by recognition between cells, such as cancer metastasis, immune diseases, inflammation, etc. by blocking the recognition between cells mediated by carbohydrates.

And also, carbohydrate-specific peptides of the present invention can be used as s diagnostic kit since their affinity is so strong as under micromol that they can distinguish the target cells having specific carbohydrates even if the cell number is low and carbohydrates are not widely distributed on the cell surfaces. In fact, sLeX used in examples of the present invention is known to widely distribute especially on cancer cells. When normal cells are turned to be abnormal cancer cells, sLeX can be detected a lot on cell surfaces. Thus, using those peptides, which can recognize sLeX makes it possible to diagnose cancer at the early stage.

The diagnostic kit of the present invention includes peptides of the present invention as the primary protein recognizing carbohydrates on cancer cells, antibody against the primary protein which was prepared by binding marker like horseradish peroxidase (HRP) as a secondary antibody, and substrate solution containing color development material which induce color development by reaction with the marker.

The above diagnostic kit is highly specific for the detection of cancer cells from the early stage since its primary peptides recognizing target carbohydrates have a strong affinity.

The secondary antibodies have been bound with the marker, and horseradish peroxidase (HRP) or alkaline phosphatase could be used as a marker.

Substrate solution, which induces color development by the reaction with the above marker of the secondary antibody, consists of buffer solution and color development material such as tetramethyl benzidine, 4-chloro-1-naphtol- or hydrogen peroxide. Substrate solution disintegrates markers bound to the secondary antibodies for the color development. The existence and the amount of antigen can be confirmed by measuring the level of color development.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Selection of Peptides

As described above, in order to obtain molecules having strong binding capacity to carbohydrates using repetitive structure of peptide, sialyl Lewis X (sLeX) existing in tumor cells or inflammation response cells was selected as a target, and a peptide binding to the sLeX well was selected by using peptide phage library and biopanning method. Particularly, sLeX-BSA(Oxford Glycoscience) was added into 0.1 M $NaHCO_3$(pH 8.6) buffer solution until the concentration reached to 100 µg/ml. 150 µl of the above solution(sLeX-BSA 0.1 M $NaHCO_3$) was loaded into one well of 96-well plate, and 150 µl of BSA 0.1 M $NaHCO_3$(pH 8.6) was also loaded into the other well. The well plate was shaken to soak completely, and left for overnight at 4° C. The solution in 96-well plate was washed, followed by adding 200 µl of blocking solution(0.1 M ethanol amine, 0.1 M $NaHCO_3$, pH 8.6) into the wells, and then the plate was left for overnight at 4° C. After blocking solution was removed from the 96-well plate, the plate was washed with 200 µl of TBS-T(50 mM Tris-HCl, pH 7.5, 150 mM NaCl, 0.1% [v/v] Tween-20). The above washing procedure was repeated 6 times to remove unfixed compounds completely.

Phage(Pharmacia, USA) was diluted with 100 µl of TBS-T buffer solution, and loaded into the well containing buffer solution only, followed by 20 minutes shaking at room temperature. sLeX-BSA solution was transferred into the well fixed with BSA, and the plate was shaken for 30 minutes at room temperature. Solution was removed from the 96-well plate, and the plate was washed with 200 µl of TBS-T buffer solution 10 times. 200 µl of sLeX-TBS solution(1 mg/ml) was added thereto, followed by shaking for 30 minutes, and finally phage which showed high affinity to sLeX was extracted from well. The above solution was transferred into 1.5 ml Eppendorf tube, and the obtained phage was amplified as follows.

180 µl of extraction solution was loaded into 3 ml of ER2537 culture solution($OD_{600}$=0.2–0.3) and cultured for 4.5 hours at 37° C. while shaking with 250 rpm. The above solution was transferred into two 1.5 ml tubes, followed by centrifugation for 10 minutes with 10,000 rpm. After that, the cells were precipitated and the supernatant was transferred into a new tube. The above solution was centrifuged for 5 minutes again, and 80% of supernatant was transferred into a new tube. ⅙ volume of PEG/NaCl(20%[w/v] polyethylene glycol-8000, 2.5 mM NaCl) was added thereto, and left it for overnight at 4° C. On the next day, centrifugation was performed for 15 minutes at 4° C. with 10,000 rpm. As a result, the phage was precipitated into the bottom of the tube as a white clot. The clot was resolved in 1 ml of TBS(50 mM Tris-HCl, pH 7.5, 150 mM NaCl) buffer solution, followed by centrifugation for 5 minutes at 4° C. with 10,000 rpm. The supernatant was transferred into a new tube and ⅙ volume of PEG/NaCl solution was added thereto, and left it for 1 hour in an ice-bath. Centrifugation(4° C., 10,000 rpm, 10 minutes) was performed again and the supernatant was removed carefully. The phage clot in the bottom of the tube was resolved in 200 µl of TBS, 0.02% $NaN_3$. The amplified phage obtained above was diluted with various concentrations, and the proper concentration was calculated as follows.

1 μl of phage solution was diluted with $\frac{1}{10}^9$, $\frac{1}{10}^{10}$ and $\frac{1}{10}^{11}$ each, and added in 200 μl of ER2537 culture solution ($OD_{600}$=0.3–0.4), and left it for five minutes at room temperature. Agarose top(10 g bacto-trypton, 5 g yeast extract, 5 g NaCl, 1 g $MgCl_2.6H_2O$, 7 g agarose/L) was melted in electric oven and each 3 ml of agarose top was transferred into 3 tubes(15 ml).

200 μl of ER2537 culture solution was added into the agarose top solution and shaken. The above solution was poured onto agar plate(10 g bacto-trypton, 5 g yeast exact, 5 g NaCl, 15 g bacto agarose/1 L) loaded with 4 μl of IPTG(Isopropylthio-β-D-galactoside, 200 mg/ml) and 40 μl of x-gal (20 mg/ml). The above plate was left for 5 minutes at room temperature and cultured for overnight in the 37° C. incubator. On the next day, the numbers of blue-colored plaques were counted and the proper concentration of amplified phage was calculated. About $5\times10^5$ phages were diluted with 100 μl of TBS-T buffer solution and added into the well fixed with sLeX, followed by biopanning. This biopanning procedure was repeated three times.

After three times biopanning, 1 μl of phage extraction solution was diluted with $\frac{1}{10}^4$, $\frac{1}{10}^5$ and $\frac{1}{10}^6$, and the diluents were mixed with melted agarose top solution. The above mixture was poured onto the agar plate loaded with IPTG and X-gal, and cultured for overnight. 10–15 plaques were picked from the plate in which fewer than 100 plaques were produced. Plaques were put into 2 ml of ER2537 culture solution ($OD_{600}$=0.2–0.3) and cultured for 5 hours at 37° C. while shaking with 250 rpm. 500 μl of the above culture solution was mixed with 1 ml of glycerol and stored at −70° C. The remnants were transferred into a 1.5 ml tube, followed by centrifugation for 10 minutes with 10,000 rpm. Only the supernatant was transferred into a new tube again. After 5 minutes centrifugation, 1 ml of the supernatant was transferred into a new tube, and 300 μl of PEG/NaCl was added thereto. After mixing carefully, the tube was left for ten minutes at room temperature, and centrifuged for 10 minutes with 10,000 rpm, followed by removing solution only.

100 μl of Iodide buffer solution(10 mM Tris-HCl, pH 8.0, 1 mM EDTA, 4 M NaI) and 250 μl of ethanol were added into the above tube and mixed well. After leaving for 10 minutes at room temperature, centrifugation (10,000 rpm, 10 minutes) was performed to remove solution. 100 μl of 70% ethanol was added and centrifuged again (10,000 rpm, 5 minutes). The supernatant solution in the tube was removed and dried completely. Finally, phage nucleic acid was prepared by dissolving white clot in the bottom of the tube with 15 μl of TE(10 mM Tris-HCl, pH 8.0, 1 mM EDTA).

Using the above phage nucleic acid as a template, PCR was performed. For the PCR, −28 g||| base sequence origin and ABI PRISM™ Dye Terminator Cycle Sequencing Ready Reaction Kit with AmpliTag DNA Polymerase FS(part #402080, Perkin Elmer, USA) were used. Amplification was performed using a Perkin-Elmer Model 2400 heat cyclacer (Perkin Elmer, USA) by 25 cycles as follows: 98° C. for 10 seconds, 50° C. for 5 seconds and 60° C. for 5 minutes. PCR mixture was composed of Terminator Ready Reaction Mixture 8.0 μl, single chain phage nucleic acid 9 μl (100–150 ng), −28 g||| base sequence origin represented by the SEQ. ID NO. 2 (1 μM) 3 μl and the total volume of PCR mixture was 20 μl. After PCR, base sequence was confirmed by using ABI 373 automatic sequencer (Applied Biosystems, USA).

As a result, it was confirmed that the binding capacity of the peptide represented by the SEQ. ID NO.1 and composed of 12 amino acids to sLeX was better than that of the other peptides.

Example 2

Construction of Peptides 12-mer peptide selected in <example 1> could bind to sLeX, but the binding capacity was not high. To increase the binding capacity of the above peptide, octopus-like peptide consisting of tandem repeat was constructed.

Particularly, dimer having structure of <Chemical Formula 2>, which is combined with two monomers having structure of <Chemical Formula 1>, which is combined 12-mer peptide with lysine and tetramer having structure of <Chemical Formula 3>, which is combined with four monomers were constructed. And, lysine was fixed onto the surface of solid.

<Chemical Formula 1>

<Chemical Formula 2>

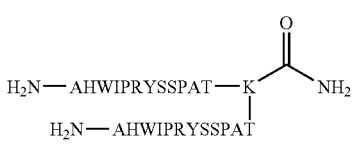

<Chemical Formula 3>

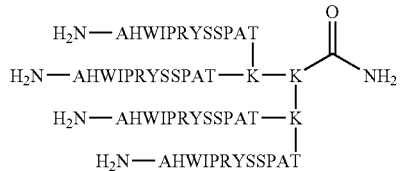

Peptides were synthesized by solid-phase peptide synthesis method in Korea Basic Science Institute. During the synthesis procedure of dimer and tetramer, 2 free amino group was located at N-terminal by using Fmoc-Lys (Fmoc)-OH at C-terminal. And the peptide dimer was constructed with the above intermediate. When the Fmoc-Lys (Fmoc)-OH was further applied to the above intermediate, 4 free amino groups can be existed at N-terminal. Thus, tetramer could be constructed by binding peptide to that point repeatedly. Therefore, tetramer was synthesized by the same method in <example 1>, which was used for monomer synthesis except that the number of N-terminal was increased with lysine.

Example 3

Purification of Peptides

Synthesized peptides were bound with resin. So, peptides were needed to be separated from resin by 2 hours treating with 5 ml of cleavage solution(2.5% thioanisole, 2.5% water, 95% trifluoracetic acid). Excessive TFA(trifluoroacetic acid) was evaporated with $N_2$, and 50 ml of diethyl ether(−20° C., pre-chilled) was added to peptide solution, followed by leaving it for overnight at −20° C. After then, precipitated peptides were obtained by centrifugation, and purification was performed by HPLC (high-performance liquid chromatography) using $C_{18}$ column. Water containing 0.1% TFA and acetonitrile were used as HPLC solvents. Particularly, peptides were dissolved in DMSO(dimethyl sulfoxide) to the concentration of 10 mg/ml, and then, 200 µl of peptide solution was loaded into the HPLC tube each time. Purification was accomplished by using a program, which changes acetonitrile composition from 5% to 95% for 30 minutes. At that time, flow rate was 3 ml/min. and detection wave-length was 220 nm.

As a result, peptides of the present invention were mostly purified around 20–30 minutes. Purified peptide solution was reduced the pressure to evaporate acetonitrile and TFA, and freeze-dried. The molecular weight of peptide was confirmed with mass spectrometry.

Experimental Example 1

Measurement of Binding Capacity of Peptides

To measure the binding capacity of peptides, BIAcore was used. CM5 made by gold and protruded with CM-dextran layer and carboxylic acid group was used as a chip. BSA (Oxford Glyco Science, USA) binding with sLeX was used as a ligand for fixing.

At first, chip surface was stabilized with 100 mM HEPES buffer solution (pH 8.0), and activated with the mixture of 0.4 M EDC (1-ethyl-3-[3'-dimethylaminopropyl]carbodiimide) and 0.1 M NHS (N-hydroxysuccunimide). And then, sodium acetate buffer(10 mM, pH 4.0) containing 0.05 mg/ml of sLeX-BSA or BSA was injected and fixed onto the surface of CM5 chip until the value of RU reached to 6,000. Chip surface remaining active state was substituted with 1.0 M ethanolamine. Target molecules were bound to CM5 chip, and binding buffer (0.01 M HEPES, 0.15 mM NaCl, 3 mM EDTA, 0.005% polysorbate 20, pH 7.4) was flowed on the chip surface for equilibration, and finally, bindng capacity was determined by flowing binding buffer containing peptides according to the concentrations. At that time, peptides were combined with their targets with different speed and slope according to the affinity of peptides and target molecules and the affinity between target molecules was measured from the each result.

In the results of monomer and dimer, Kp against sLeX was 25.4 mM and 0.79 mM, respectively. Thus, it was confirmed that the binding capacity of dimer was increased about 33 times stronger than that of monomer.

And also, sLeX-BSA was fixed onto the surface of CM5 chip, followed by flowing the same amount of monomer, dimer and tetramer, and the amount of peptides bound to sLeX was confirmed with the size of BIAcore sensorgram.

Figure 1:
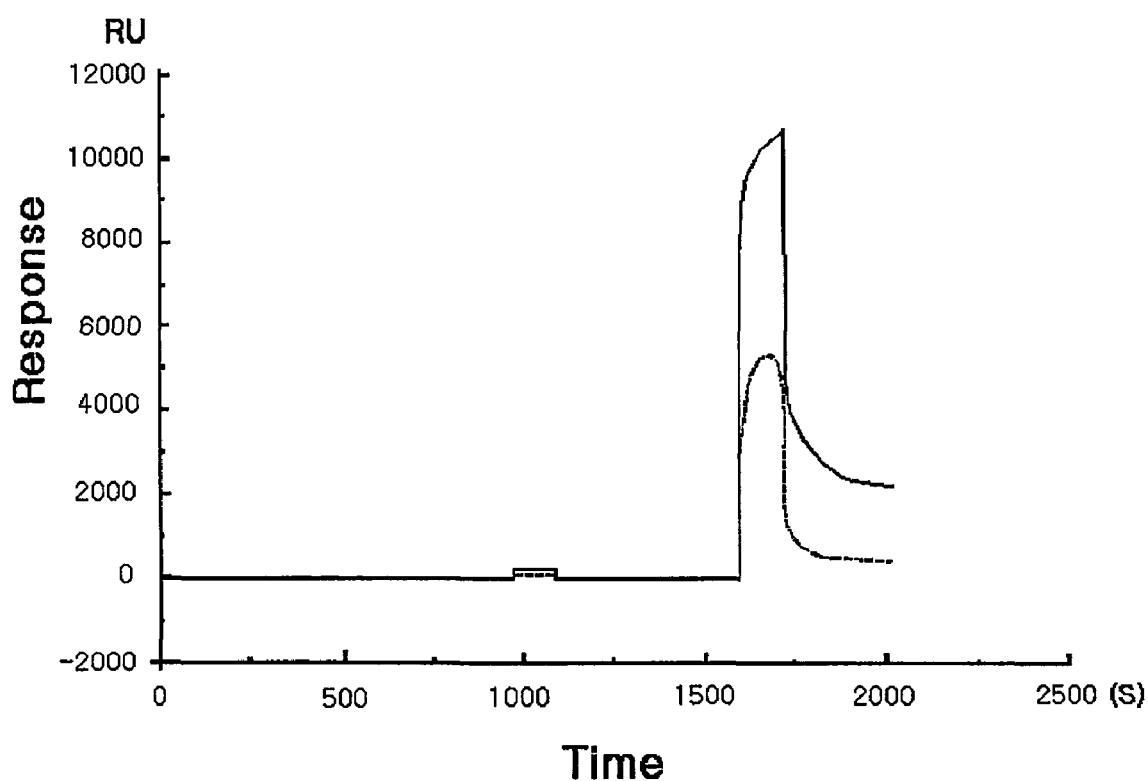
FIG. 1 is the graphs confirmed by BIAcore, which show different joint intensity of monomer, dimer and tetramer binding to sLeX specifically. The joint intensity was measured by letting monomer, dimer and tetramer flow thereto with 62.5 µM in order.

As shown in FIG. 1, the amount of peptides bound to the chip fixed with sLeX-BSA was more than that of peptides bound to the chip fixed with BSA only. It means that the peptides of the present invention could bind to sLeX specifically. Though monomer, dimer and tetramer were flowed with same concentration(62.5 µM), binding levels were different. The strength of binding was converted into the height of sensorgram, resulting in 16(monomer), 147(dimer) and 5570(tetramer) RU. Especially, tetramer showed 40 times stronger binding strength compared to that of dimer. Conclusively, binding capacity of peptides of the present invention was increased as the number of multiple bonds.

Experimental Example 2

Competitive Binding of Peptides Using HL60 Hela Cell

P-selectin can combined with sLeX carbohydrate-rich HL60 cell specifically. To investigate the possibility that peptides of the present invention can inhibit the specific recognition between selectin and sLeX carbohydrate, the present inventors performed below experiment.

At first, P-selectin(pH 9.2, Calbiochem, USA) dissolved in 50 mM $NaHCO_3$ buffer solution(10 µg/ml) was loaded into each well(250 ng) of well-plate. Selection was fixed by leaving the plate for overnight at 4° C. BSA solution was prepared with same concentration and method, and used as a control. Secondly, TNF-α (LG biotech, Korea) was added into HL60 cell culture solution($10^6$/ml, 150 mM NaCl, 10 mM HEPES, 1 mM $CaCl_2$, 1 mM $MgCl_2$, pH 7.4) to the concentration of 10 ng/ml. The above solution was left for 20 hours and 50 µl of the solution was transferred into a tube, which was left for 30 minutes at room temperature. The solution was washed with PBS containing 1 mM $CaCl_2$, 1 mM $MgCl_2$ and DEPC until floating cells were totally removed.

To verify binding between peptides of the present invention and cells, peptides and cells were pre-mixed and left for 30 minutes at room temperature. The above mixture was added into well plate fixed with selectin or BSA, and the number of binding cells was calculated and recorded with inverted microscopy. While changing the location of the microscopy, 5 times experiments were performed and the mean value was obtained. Cell number was controlled to fewer than 300 to minimize errors.

As shown in FIG. 2, peptides of the present invention inhibited binding between P-selectin and HL60 cells. Especially, inhibitory effect of tetramer was higher than that of dimer. This result was consistent with the result of <Experimental Example 1>.

Conclusively, it was confirmed that the peptides of the present invention could recognize carbohydrates specifically, and made by dimer or tetramer by multiple combination, resulted that it has a very strong affinity under micromol. Peptide having strong affinity of the present invention can be used for the treatment of diseases mediated by recognition between cells and used as a diagnostic kit, which diagnoses diseases by confirming the existence of any specific carbohydrate.

INDUSTRIAL APPLICABILITY

As described hereinbefore, peptides of the present invention could be used as a treatment against inflammation, immune-disease and metastasis of cancers, which are the diseases mediated by recognition between cells, owing to its ability to shut off recognition between cells by the competitive inhibition effect in vivo. And the peptides of the present invention can be used as a diagnostic kit, which diagnoses by confirming the existence of specific carbohydrate. Especially, the peptides having a strong affinity to carbohydrates of the present invention can be used for diagnosis of early stage cancer because it can recognize specific cells even if the cells are few or carbohydrates are not widely distributed on cell surfaces.

What is claimed is:

1. A preparation method of a multimer having affinity under micromol to carbohydrates existing on the cell surfaces comprising the following steps: 1) selecting a peptide, which can bind specifically to carbohydrates existing on cell surfaces from a peptide library; 2) constructing of a multimer of the peptide; 3) measuring a binding affinity of the multimer to the carbohydrates; and 4) determining whether the binding affinity is under micromol.

2. The preparation method as set forth in claim 1, wherein the multimer is constructed by using an amino acid having at least 2 amino groups.

3. The preparation method as set forth in claim 2, wherein the amino acid having at least 2 amino groups is selected from the group consisting of lysine, and ornitine.

4. The preparation method as set forth in claim 1, wherein the carbohydrate existing on the cell surface is a carbohydrate compound cancer-marker.

5. The preparation method as set forth in claim 4, wherein the carbohydrate compound cancer-marker is selected from the group consisting of sLeX, LeX, sLeA and LeA.

6. The preparation method as set forth in claim 1, wherein the peptide has the amino acid sequence represented by the SEQ. ID. NO: 1.

7. The preparation method as set forth in claim 1, wherein the peptide is selected by a method selected from the group consisting of phage display method, position scanning method and deconvolution method.

* * * * *

SEQUENCE LISTING

<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: synthetic peptide which have a strong
      affinity to carbohydrate

<400> SEQUENCE: 1

Ala His Trp Ile Pro Arg Tyr Ser Ser Pro Ala Thr
1               5                   10

<210> SEQ ID NO 2
<211> LENGTH: 21
<212> TYPE: DNA
<213> ORGANISM: Artificial Sequence
<220> FEATURE:
<223> OTHER INFORMATION: primer

<400> SEQUENCE: 2
gtatgggatt ttgctaaaca a                                              21